US006828153B2

(12) United States Patent
Jonker et al.

(10) Patent No.: US 6,828,153 B2
(45) Date of Patent: Dec. 7, 2004

(54) METHOD AND APPARATUS FOR MEASURING THE ACCESSIBILITY OF POROUS MATERIALS WITH REGARD TO LARGE COMPOUNDS

(75) Inventors: Robert Jan Jonker, Amsterdam (NL); Paul O'Connor, Hoevelaken (NL); Hendrikus Nicolaas Johannes Wijngaards, Edam (NL)

(73) Assignee: Akzo Nobel N.V., Arnhem (NL)

( * ) Notice: Subject to any disclaimer, the term of this patent is extended or adjusted under 35 U.S.C. 154(b) by 195 days.

(21) Appl. No.: 10/158,795

(22) Filed: May 31, 2002

(65) Prior Publication Data

US 2002/0187555 A1 Dec. 12, 2002

(30) Foreign Application Priority Data

Jun. 5, 2001 (EP) .............................................. 01202147

(51) Int. Cl.$^7$ .............................................. G01N 31/10
(52) U.S. Cl. ......................... 436/37; 436/29; 436/139; 436/140
(58) Field of Search .......................... 436/37, 29, 139, 436/140, 164, 172

(56) References Cited

U.S. PATENT DOCUMENTS

| | | | | |
|---|---|---|---|---|
| 3,900,291 | A | 8/1975 | Francardi | .................. 23/253 R |
| 4,762,010 | A | 8/1988 | Borghard et al. | .......... 73/865.5 |
| 5,109,714 | A | 5/1992 | Slomka et al. | ............. 73/865.5 |
| 5,194,921 | A * | 3/1993 | Tambo et al. | ................ 356/432 |
| 6,171,991 | B1 | 1/2001 | Stamires et al. | ............ 501/141 |
| 6,376,405 | B1 | 4/2002 | Stamires et al. | .............. 502/73 |

FOREIGN PATENT DOCUMENTS

| | | | | |
|---|---|---|---|---|
| SU | 1 325 330 | 7/1987 | .......... G01N/15/08 |
| WO | 01/12550 | 2/2001 | ............. C01F/7/00 |

OTHER PUBLICATIONS

Romero et al. "Separation of FCC catalyst on skeletal density and Akzo Accessibility Index", http://www.akzonobel–catalysts.com/html/FCC/technicalinformation/Articles, placed on–line Nov. 20, 2002.*

"NPRA Question & Answer Sessions on Refining and Petroleum Technology—Oct. 2001", Catalysts Courier 46 on–line.*

Hakuli et al. "Understanding FCC Catalyst Architecture and Accessibility", Akzo Nobel Catalysts Symposium, Jun. 05, 2001.*

Klunder et al. in "Chemical, Biochemical, and Environmental Fiber Sensors V", published 1994, pp. 186–191 (Abstract) http://www.spie.org/web/abstracts/2000/2068.html.*

European Search Report for: EP 01 20 2147; dated: Nov. 19, 2001.

Saint–Just; *Catalyst Characterization by Adsorption of Petroleum Asphaltenes in Solution*; Ind. Eng. Chem. Prod. Res. Dev. 1980, vol. 19; pp. 71–75.

Yang et al.; *Hindered Diffusion of Coal and Petroleum Asphaltenes in a Supported Hydrotreating Catalyst*; Am. Chem. Soc., Div. Fuel Chem., vol. 41, 1996, pp. 1013–1019.

Yudin et al.; *Crossover Kinetics of Asphaltene Aggregation in Hydrocarbon Solutions*; Physica A, vol. 251; 1998, pp. 235–244.

Satterfield et al.; *Restricted Diffusion in Liquids within Fine Pores; AIChE* Journal, vol. 19, , No. 3, 1973, pp. 628–635.

Prashner et al.; *Liquid Diffusion in Microporous Alumina Pellets; AIChE* Journal, vol. 23, No. 3, 1977, pp. 303–310.

Ruthven; *Measurement of Diffusion in Microporous Solids*; Separation Technology; vol. 1, 1994, pp. 1–25.

Derwent Abstract No.: 1988–069235, abstracting Russian Patent No.: SU 1 325 330.

* cited by examiner

*Primary Examiner*—Yelena G. Gakh
(74) *Attorney, Agent, or Firm*—Louis A. Morris

(57) ABSTRACT

The present invention provides a method for testing the accessibility of porous materials with regard to large, often high-molecular weight compounds and correlating said accessibility to the porous material's accessibility under conditions of use, i.e. the application conditions.

17 Claims, No Drawings

METHOD AND APPARATUS FOR MEASURING THE ACCESSIBILITY OF POROUS MATERIALS WITH REGARD TO LARGE COMPOUNDS

CROSS REFERENCE TO RELATED APPLICATION

This application claims priority from European Patent Application Number EP01202147.3, filed Jun. 5, 2001.

BACKGROUND OF THE INVENTION

1. Field of the Invention

The present invention relates to a method and apparatus for testing the accessibility of porous materials with regard to compounds comprising large molecules.

2. Prior Art

The accessibility of porous materials with regard to large, often high-molecular weight compounds is an important feature, for instance in catalysis. The accessibility of porous material can change substantially during its preparation and processing. For example, during preparation or processing of the material diffusion barriers—either internal (pore plugging, small pores, etc.) or external (e.g. skin formation)—can be formed, thereby decreasing the accessibility of the material. Important factors that influence the formation of these barriers are the properties of the constituting components (morphology, size, reactivity, crystallinity, etc.) and the applied conditions (pH, T, time, etc.). Diffusional barriers can be formed during the catalyst's life time or regeneration, due to sintering, contamination with metals (e.g. Fe, V, Ca, Na) or coke, or the formation of a low-accessibility skin on the catalyst's surface. The formation of diffusional barriers and, as a consequence, a reduction in accessibility can lead to a major decrease of activity in the various catalytic reaction systems.

With the formation of diffusional barriers via a low-accessibility skin on the outer surface of the porous materials the entrance to the pores is narrowed, while the total pore volume will hardly be affected. This skin will only restrict relatively large and rigid molecules from entering the pores. Therefore, common static techniques to study the pore size of porous materials, such as Hg-porosity measurements, nitrogen adsorption, etc., are not suitable for showing the presence of such a skin. In order to monitor skin formation and the accessibility of the pores with regard to large, often high-molecular weight compounds and to be able to develop catalysts with high accessibility, it is important that this accessibility can be measured fast, easily and accurately in a dynamic way. Moreover, it is a necessity that the test results can be correlated to the accessibility of the porous materials under conditions of use. In this specification, these conditions will be referred to as the application conditions.

A method for measuring the uptake of asphaltenes, i.e. Kuwait long residue, by hydrotreating catalysts is disclosed by J. Saint-Just, Ind. *Eng. Chem. Prod. Dev.* Vol. 19, 1980, pp. 71–75. This measurement is performed by circulating an asphaltene-containing toluene solution through a fixed catalyst bed (supported by glass wool) and a spectrophotometer. The decrease in absorbance at 550 nm is measured as a function of time.

There are several drawbacks to this method. The first is that the flow of a solution over a fixed catalyst bed will cause mainly chromatographic aspects i.e. adsorption effects such as adsorption capacity and competitive adsorption to be measured, rather than penetration, diffusion or accessibility effects. Although these effects will all influence the breakthrough time of the compounds, they cannot be separated and individually determined by this method. As will be explained later in this specification, determination of the diffusion effects is a prerequisite for correlation of the test results to the application conditions of the porous materials. Secondly, toluene bubbles are formed by the forced flow of toluene through the catalyst bed and the supporting glass wool. To prevent these bubbles from causing erratic reading of the absorbance by the spectrophotometer, a reservoir is needed to trap them. Further, the results of this method are only correlated to the uptake of vanadium-containing compounds by the catalyst. The publication of Saint-Just does not provide a method where the results are correlated to the accessibility of the catalyst under conditions of use.

X. Yang et al., *Am. Chem. Soc., Div. Fuel Chem.*, Vol. 41, 1996, pp. 1013–1019, disclose a study on the hindered diffusion of asphaltenes in $NiMo/Al_2O_3$ catalysts, i.e. hydroprocessing catalysts. To this end, catalyst particles were added to a stirred vessel containing a solution of asphaltenes in THF. Periodically, samples were taken manually and the asphaltene concentration in these samples was measured by size exclusion chromatography (SEC). This publication does not provide a method where the accessibility of the catalyst is tested and correlated to the catalyst's accessibility under conditions of use.

SUMMARY OF THE INVENTION

In one embodiment, the present invention comprises a method for testing the accessibility of porous materials with regard to compounds comprising large molecules by:

a) adding the porous material to a stirred vessel containing probe molecules dissolved in a solvent, b) periodically analyzing the concentration of the probe molecule in the solution, and thereby measuring the probe molecule uptake, and c) correlating the uptake to the accessibility of the porous material.

In a second embodiment, the present invention comprises an apparatus for performing the above method comprising a vessel provided with stirring means, a detector, a pump, and tubes connecting these elements.

In a third embodiment, the present invention is a method for screening catalysts comprising aging a fresh catalyst followed by quantifying the Akzo Accessibility Index according to a method wherein the probe molecule uptake is correlated to the accessibility of the porous material by plotting the relative concentration of the probe molecule against the square root of time, with the Akzo Accessibility Index (AAI) being calculated from the initial slope of this plot.

Other embodiments of the invention comprise details relating to various steps in the method and elements of the apparatus, all of which are described in detail herein.

DETAILED DESCRIPTION OF THE INVENTION

The present provides a method for testing the accessibility of porous materials with regard to compounds comprising large molecules. The term "large molecules" is intended to mean molecules that are of relatively large size, preferably rigid, and often of high-molecular weight. The method correlates said accessibility to the accessibility of the porous material under conditions of use, i.e. the application conditions. In particular, it provides a method for testing the accessibility of porous materials with particle sizes down to 10 microns.

The method comprises adding the porous material to a stirred vessel containing the large, often high-molecular weight compounds (hereinafter referred to as probe molecules) dissolved in a solvent and periodically analyzing the concentration of the probe molecule compound in the solution. This analysis can be performed automatically.

In a preferred embodiment the automatic analysis is performed by circulating the dissolved probe molecules between the stirred vessel and a detector. In order to avoid porous material circulating through the system, the stirred vessel's exit may be provided with a filter.

In another preferred embodiment the automatic analysis is performed by a probe inside the stirred vessel which probe is connected to a detector, in other words, the analysis is performed in situ.

The invention also relates to an apparatus for performing this method. Preferred embodiments of the apparatus comprise a vessel provided with stirring means, a detector, a pump, and tubes connecting these elements, or a vessel provided with stirring means and a probe connected to a detector.

Most bulk catalytic processes, such as hydroprocessing (HPC) or fluid catalytic cracking (FCC), are conducted at high temperatures and in the gas phase. Therefore, if we want to study the accessibility of for instance HPC or FCC catalysts with regard to large, rigid and/or high-molecular weight compounds, the tests performed must be correlated to HPC or FCC processing conditions. With the accessibility test according to the present invention, and in contrast to the prior art tests mentioned above, this is possible. Although the method of the present invention measures the accessibility of porous materials with regard to large, often high-molecular weight compounds in the liquid phase, the results can be related to diffusion behaviour at different temperatures, pressures, and phases by the use of dimensionless parameters.

In order to be able to relate the results obtained in the liquid phase to diffusion behaviour at different temperatures and phases, it is necessary to describe the diffusion process in dimensionless parameters like relative concentration and dimensionless time (J. Crank, *The Mathematics of Diffusion*, Clarendon Press, Oxford, 1975). The relative concentration of the high-molecular weight compound is its concentration at a certain point in time, divided by its concentration at the start of the test. The dimensionless time is known as the Fourier number and defined as $(D_{\mathit{eff}} \cdot t)/(d_p^2)$, wherein $D_{\mathit{eff}}$ is the effective diffusivity in the porous material, t is the time, $d_p$ is the catalyst particle diameter. Plotting the relative concentration against the Fourier Number results in a universally applicable curve, hereinafter referred to as the universal diffusivity curve. Subtracting from unity gives the uptake. Said universal diffusivity curve containing only dimensionless parameters is independent of phase and temperature. The effective diffusivity is composed by the bulk diffusion factor in free solution and the morphology factor of the porous material. The bulk diffusion factor being constant for a certain porous material, the effective diffusivity gives a measure of the morphology factor, and thus the accessibility of the porous material.

Upon contacting the porous material with the dissolved probe molecule the concentration of this compound will decrease. This decrease is dependent int. al. on the time, the ratio of the amount of solution to the amount of porous material, the bulk diffusivity of the probe molecule in free solution, the size of the probe molecule, and the morphology of the porous material, e.g. its tortuosity, particle geometry and size, porosity, total pore volume, pore size distribution, pore geometry, diffusion barriers, and adsorption capacity.

The description of the uptake curve is mathematically complex, as the decrease in the concentration of the high-molecular weight compound and the specific geometry of the porous material have to be taken into account. However, at the beginning of the uptake, i.e. at low Fourier numbers, the description becomes relatively simple and a relation between the uptake and the effective diffusivity can be established.

The accessibility of porous materials with regard to large, often high-molecular compounds according to the present invention is quantified by the Akzo Accessibility Index (AAI). The relative concentration of the high-molecular weight compound in the solution in percentage can be plotted against the square root of time in minutes. The AAI is defined as the initial slope of this plot. It can be determined manually by drawing the best possible tangent of the steepest first part of the curve. The AAI can also be determined automatically by curve fitting the first part (i.e. the first 4 minutes) of the relative concentration (C) versus the square root of the time (t) curve with a second order polynomial:

$$C = 100 + a \cdot \sqrt{t} + b \cdot (\sqrt{t})^2.$$

The AAI is now defined as AAI=−a.

The AAI is proportional to the square root of the effective diffusivity. As mentioned above, the effective diffusivity is composed by the bulk diffusion factor in free solution and the morphology factor of the porous material. The bulk factor being constant, the effective diffusivity gives a measure of the morphology factor. With the effective diffusivity the relative position of the morphology factor of a certain porous material in the universal diffusivity curve can be determined. As the morphology factor is a property of the porous material (independent of the phase where diffusion takes place), a proper ranking in accessibility (the AAI) can be given which is also applicable to other conditions in which the porous material is employed, i.e. the application conditions.

The present invention offers a way to automatically or manually measure the concentration decrease of the dissolved probe molecule in the presence of porous materials. When measuring automatically, the sampling frequency can be as high as four measurements per second, which offers accurate determination of the initial concentration decrease. Automatic measurements allow high-resolution measurements. In high-resolution measurements it is possible to measure small accessibility differences over a large range of accessibilities. In those cases the form of the diffusivity curve provides information on the underlying mechanisms of the resistance to mass transfer. Said high resolution measurements can, for instance, be used in catalyst development. On the other hand, it is also possible to use the method according to the invention for fast, low-resolution testing. This type of testing can be used for in-field testing of E-cat samples and for fast screening of large sets of samples. For fast, low-resolution testing the concentration can also be measured manually.

The porous materials of which the accessibility can be measured by the method according to the present invention can be catalysts, catalyst additives, carriers, adsorbents, and the like, provided that the high-molecular weight compound is capable of adsorbing on the surface of the porous material. If this compound were not to adsorb on the porous material, its concentration decrease would only depend on the diffusivity, which process is too fast to be measured alone. Further, care must be taken that the ratio of the catalyst amount to the amount of solution is realistic; the ratio amount of catalyst/amount of solution should be chosen such that a measurable uptake takes place.

The accessibility of porous materials with various particle sizes, ranging from 40 to 5,000 microns, can be measured. For instance, the accessibility of both HPC and FCC catalysts can be measured.

Although the accessibility of materials with various particle sizes can be measured, the AAI value depends on the particle size of the material. In fact, the AAI is inversely proportional to the particle size. This can be understood from the fact that at constant weight with increasing particle size the outer surface available for adsorption will decrease. Therefore, in order to compare the accessibility of various materials, it is advisable to use a specified sieve fraction of the material in question. Typical examples of suitable sieve fractions include 45–53 micron, 53–63 micron, 63–75 micron, and 53–75 micron fractions.

The AAI value thus is linearly proportional to the amount of porous material. With increasing amounts the available outer surface will increase, leading to higher AAI values. Analogous to the remark above, this amount should be kept constant upon comparing the AAI of different materials. The preferred amount of porous material in the high-molecular weight compound-containing solution is 0.5 to 5 wt %.

The large, often high-molecular weight compounds of which the accessibility can be measured with the method according to the invention may be the same as the molecules that are employed as probe molecules, but in any event, the uptake of the probe molecules will be indicative of the accessibility of the porous materials with regard to the large molecules.

Suitable probe molecules (and contemplated compounds in the method of the invention) are large in size (molecular weights varying from about 250 to about 50,000) and show a tendency to adsorb on the inner surface of the porous material. Their amount must be detectable with a reasonable signal to noise ratio. If the probe molecule is not detectable per se, its detectability can be accomplished by modifying the probe with functional groups.

Examples of suitable probe molecules are porphyrines, asphaltenes, cross-linked polymers, such as polystyrenes, aramids, branched alkanes, including dendrimers, steroids, chlorophyl, aconitine, bebeerine d, dextranes, carpaine-(d) (4754), glucose, silanes, bucky balls, organometal complexes, inorganic and organic metal compounds. Preferred are porphyrines and asphaltenes, especially when measuring the accessibility of catalysts, because they resemble compounds encountered in catalytic operations.

Porphyrines are polycyclic, highly unsaturated compounds which contain four nitrogen atoms. An example of a porphyrine suitable for use in the method according to present invention is tetraphenyl porphyrine.

Asphaltenes can be defined as substances which are precipitated from oil samples by the addition of a 40-fold excess of n-heptane and are soluble in pure toluene (J. G. Spegt, S. E. Moschopedis, *Symposium on the chemistry of asphaltenes,* Sep. 9–14, 1979, ACS, Washington, p. 910). The structure of asphaltenes is dependent on the type of oil they originate from. The asphaltenes preferably used in the method according to the invention are asphaltenes present in Kuwait vacuum gas oil (Kuwait VGO), which can be detected by spectrophotometry at 560 nm and have a radius of gyration between 0.2 and 1.6 nm. Asphaltenes can be fractionated by size exclusion chromatography.

Solvents which can be used in the method according to the invention are toluene or organic solvents with a polarity comparable to or lower than that of toluene. In this specification polarity is used in a chromatographic sense as defined by Snyder's Solvent polarity parameter (L. R. Snyder, *J. Chromatogr.,* 32, 223 (1974); *J. Chromatogr. Sci.,* 16, 223 (1978)). According to this definition, the polarity of toluene is 2.4

Examples of such solvents are normal or branched alkanes, such as n-pentane, n-hexane, n-heptane, iso-octane; cycloalkanes, such as cyclopentane, cyclohexane, aromatics, such as benzene, xylenes, nitrobenzene; halogenated compounds, such as FC-75, FC43, 1-chlorobutane, 2-chloropropane, bromomethane, chlorobenzene, bromobenzene, iodobenzene, fluorobenzene, methylenechloride, chloroform; ethers, such as n-butyl ether, i-propyl ether, phenyl ether, benzyl ether, ethyl ether; amines, such as triethylamine, propylamine; alcohols, such as n-octanol, i-pentanol, t-butanol, n-butanol, n-propanol, and other types of compounds, such as carbon disulphide, phenetole, tricresyl phosphate, anisole, tetrahydrofuran, ethyl acetate, acetophenone, methylethyl ketone, cyclohexanone, dioxane quinoline, pyridine, nitroethane, and acetone.

The preferred amount of solution to be used in the present method depends on the volume of the stirred vessel, and in the case of a circulating system on the volume of the tubes, the volume of the flow cell, and the flow rate. Every system will have its optimum. Typically, the total volume of the system can range from 10 to 500 ml, preferably from 30 to 100 ml. The solids to liquid ratio in the vessel can range from 0.2 to 10 wt %, preferably from 1 to 4 wt %, while the probe molecule concentration in this solution can range from 0.01 to 10 wt %, preferably from 1 to 4 wt %.

The probe molecule concentration can be measured by any suitable detector for analyzing the specific molecule. Examples of such detectors are those commonly used in HPLC systems, such as UV/Vis spectrophotometers, fluorescence detectors, refractive index detectors or electrochemical detectors. Also other principles of detection can be used, such as (near) infrared spectroscopy and RAMAN spectroscopy. Preferably, a UV/is spectrophotometer is used as detector. The wavelength of the light used depends on the nature of the probe molecule and the solvent. In the case of asphaltenes the wavelength will usually be higher than 400 nm, preferably 560 nm. The concentration of porphyrines can be measured at the wavelength near the Soret band of the porphyrines.

In a first embodiment the solution circulates between the stirred vessel and the flow cell of a detector. In a second embodiment the stirred vessel contains a probe connected to a detector in order to measure the concentration of the high-molecular compound in situ.

The invention also relates to an apparatus for measuring the accessibility of porous materials with regard to large, often high-molecular weight compounds according to the first embodiment. This apparatus comprises a stirred vessel. The vessel can simply be a beaker or any other type of (glass) reactor. Stirring of the vessel contents, i.e. the solution containing the probe molecule and the added porous material, can be performed by any kind of stirring device, such as a magnetic stirrer, a mechanical stirring device, a vortex mixer or a spinning basket.

In the first embodiment, tubes interconnect the stirred vessel and the flow cell of a detector. Circulation of the solution through these tubes is possible by way of a pump with a low hold-up volume, such as a peristaltic pump or a piston pump. The pumping rate can range for instance from 10 to 30 g/min, without affecting the AAI value. The preferred pumping rate will depend on the volume of the system and the amount of solution present in this system.

To prevent the porous material from circulating through the system, the solution leaves the stirred vessel through a filter. The apparatus will thus comprise a stirred vessel having an outlet comprising a filter, the outlet being connected via a tube to the inlet of a pump, the pump having an outlet connected via a tube to the inlet of the flow cell of a detector and the detector analyzing the solution passing through the flow cell. Optionally, the flow cell outlet may be connected via a tube to an inlet to the stirred vessel to effect recirculation.

The detector is capable of automatically analyzing the concentration of the high-molecular weight compound in the circulating solution at a frequency of at least one measurement per second. Preferably, a detector is used which is capable of conducting at least four measurements per second.

In the second embodiment, and in lieu of a detector and flow cell, the apparatus of the invention employs a probe connected to a detector, with the probe immersed in the contents of the vessel. Examples of suitable probes are optical probes (IR, RAMAN, ATR) and sensors (pH sensors, mass transducers, ion selective electrodes, calorimetric sensors, biochemical sensors).

The invention also relates to a method for screening catalysts comprising aging a fresh catalyst followed by quantifying the Akzo Accessibility Index. In a specific embodiment this method is used for FCC catalysts, which are aged under typical FCC conditions. To test the impact of contaminant metals such as Fe, V, Ca or Na, these metals can be present during aging.

Catalyst structure is important especially when the FCCU operates in a diffusion limited regime. As is illustrated in the example, the catalyst performance deteriorates very rapidly when the AAI falls below a certain value, which is typical for each unit's characteristics. This value is referred to as the "critical" AAI. Such a decrease in AAI immediately results in a rapid deterioration of the performance, such as gasoline yield, and particularly in bottoms conversion. More specifically, the specific gravity of the bottoms is also influenced by the catalyst's AAI.

The invention is further illustrated by the following example.

EXAMPLE

A 1 l solution of 15 g Kuwait VGO in toluene was prepared by heating a Kuwait VGO feed to 70° C. in an oven. 15 g of the warm Kuwait VGO were suspended in 200 ml warm toluene. The mixture was well stirred and adjusted to 1 liter with toluene. The solution was stored in the dark. 50.00 g of this solution were added to a 100 ml beaker (glass) which was connected to a peristaltic pump and a detector by tubes. The solution was stirred with a propeller stirrer at 400 rpm and the peristaltic pump was set at 21 g/min. A spectrophotometer was used as detector. This spectrophotometer was set to zero using a toluene solution.

Next, 1 g of a 53–75 micron sieve fraction of an FCC catalyst was added to the Kuwait VGO in toluene solution. Once per second the asphaltene concentration was measured by spectrophotometry at a wavelength of 560 nm.

After 5 minutes, the measurement was stopped and the absorbance was plotted versus the square root of time. The slope, i.e. the Akzo Accessibility Index (AAI), was determined.

The AAI was determined for several catalysts. For some of the catalysts the accessiblity was deliberately made worse. Said catalysts were tested in an FCCU. It was found that when the AAI decreased below 4 (the critical AAI for the FFCU), the catalyst performance was hampered, resulting in a rapid deterioration of the conversion, gasoline yield, and bottoms conversion.

What is claimed is:

1. A method for determining the accessibility of porous materials under conditions of use with regard to compounds comprising large molecules by:

a) adding the porous material to a stirred vessel containing probe molecules dissolved in a solvent, b) periodically analyzing the concentration of the probe molecule in the solution, and thereby measuring the probe molecule uptake, and c) correlating the accessibility under conditions of use to the uptake of the porous material by plotting the relative concentration of the probe molecule against the square root of time, with the Akzo accessibility Index (AAI) being calculated from the initial slope of this plot.

2. The method of claim 1 wherein the analysis is performed automatically.

3. The method of claim 2 wherein the analysis is performed by circulating the dissolved probe molecule between the stirred vessel and a detector.

4. The method of claim 2 wherein the analysis is performed by a probe inside the stirred vessel which probe is connected to a detector.

5. The method of claim 1 wherein the detector is a spectrophotometer.

6. The method of claim 1 wherein the detector is a fluorescence detector.

7. The method of claim 1 wherein the analysis is performed with a frequency of at least one measurement per second.

8. The method claim 1 wherein the probe molecules are selected from porphyrins and asphaltenes.

9. The method of claim 8 wherein the probe molecules are asphaltenes with a radius of gyration between 0.2 and 1.6 nm.

10. The method of claim 1 wherein the solvent is chosen from the group of organic solvents with a polarity comparable to or lower than that of toluene.

11. The method of claim 10 wherein the solvent is toluene.

12. The method of claim 1 wherein the porous materials are catalysts, catalyst additives or sorbents.

13. The method of claim 12 wherein the catalyst is a Fluid Catalytic Cracking (FCC) catalyst.

14. The method according of claim 12 wherein the catalyst is a hydroprocessing (HPC) catalyst.

15. A method for screening catalysts comprising porous material, said method comprising aging a fresh catalyst comprising said porous material followed by quantifying the Akzo Accessibility Index of said porous material according to the method of claim 1.

16. The method of claim 15 wherein the catalyst is an FCC catalyst and aging is performed under typical FCC conditions.

17. The method of claim 15 wherein during aging Fe, V, Ca and/or Na are present.

* * * * *

UNITED STATES PATENT AND TRADEMARK OFFICE
CERTIFICATE OF CORRECTION

PATENT NO. : 6,828,153 B2  Page 1 of 1
APPLICATION NO. : 10/158795
DATED : December 7, 2004
INVENTOR(S) : Jonker et al.

It is certified that error appears in the above-identified patent and that said Letters Patent is hereby corrected as shown below:

On the title page item (*) Notice line 3, should read -- by 287 days. --

Signed and Sealed this

Twentieth Day of February, 2007

JON W. DUDAS
*Director of the United States Patent and Trademark Office*